United States Patent
Kibrya et al.

(10) Patent No.: US 12,329,423 B2
(45) Date of Patent: Jun. 17, 2025

(54) STYLET CONTROL HANDLES AND METHODS OF USING THE SAME

(71) Applicant: NuVasive, Inc., San Diego, CA (US)

(72) Inventors: Naomi Kibrya, San Diego, CA (US); Megan Jeffords, San Diego, CA (US); Matthew Tobias Jacobs, San Diego, CA (US); Ryan Woods, San Diego, CA (US)

(73) Assignee: Nuvasive Inc., San Diego, PA (US)

( * ) Notice: Subject to any disclaimer, the term of this patent is extended or adjusted under 35 U.S.C. 154(b) by 849 days.

(21) Appl. No.: 17/645,201

(22) Filed: Dec. 20, 2021

(65) Prior Publication Data

US 2022/0192718 A1 Jun. 23, 2022

Related U.S. Application Data

(60) Provisional application No. 63/128,606, filed on Dec. 21, 2020.

(51) Int. Cl.
*A61B 17/70* (2006.01)
*A61B 17/88* (2006.01)
*A61B 17/00* (2006.01)

(52) U.S. Cl.
CPC ...... *A61B 17/7076* (2013.01); *A61B 17/7065* (2013.01); *A61B 17/7082* (2013.01); *A61B 17/8897* (2013.01); *A61B 2017/00115* (2013.01); *A61B 2017/00407* (2013.01)

(58) Field of Classification Search
CPC .................. A61B 17/7076; A61B 17/7075
See application file for complete search history.

(56) References Cited

U.S. PATENT DOCUMENTS

| | | | |
|---|---|---|---|
| 9,107,768 B2* | 8/2015 | Schell | A61F 2/4455 |
| 9,314,274 B2* | 4/2016 | Amstutz | A61B 17/7002 |
| 10,070,873 B2* | 9/2018 | Courtney, Jr. | A61B 17/1624 |
| 11,457,961 B2* | 10/2022 | Ramsay | A61B 17/1655 |
| 2007/0162046 A1* | 7/2007 | Vandewalle | A61B 17/8875 606/108 |
| 2009/0275954 A1 | 11/2009 | Phan et al. | |
| 2014/0276894 A1 | 9/2014 | Ramsay et al. | |
| 2018/0368893 A1 | 12/2018 | DiVincenzo et al. | |
| 2019/0125421 A1 | 5/2019 | Smith et al. | |
| 2019/0183516 A1 | 6/2019 | Peterson et al. | |
| 2019/0262055 A1 | 8/2019 | Haziza | |
| 2019/0269469 A1 | 9/2019 | Bush, Jr. et al. | |

* cited by examiner

*Primary Examiner* — Christian A Sevilla

(57) ABSTRACT

Disclosed herein are stylet control handles and related methods for extending and retracting a stylet during insertion of a bone anchor, and for providing a visual indication of the extent of extension of the stylet.

20 Claims, 6 Drawing Sheets

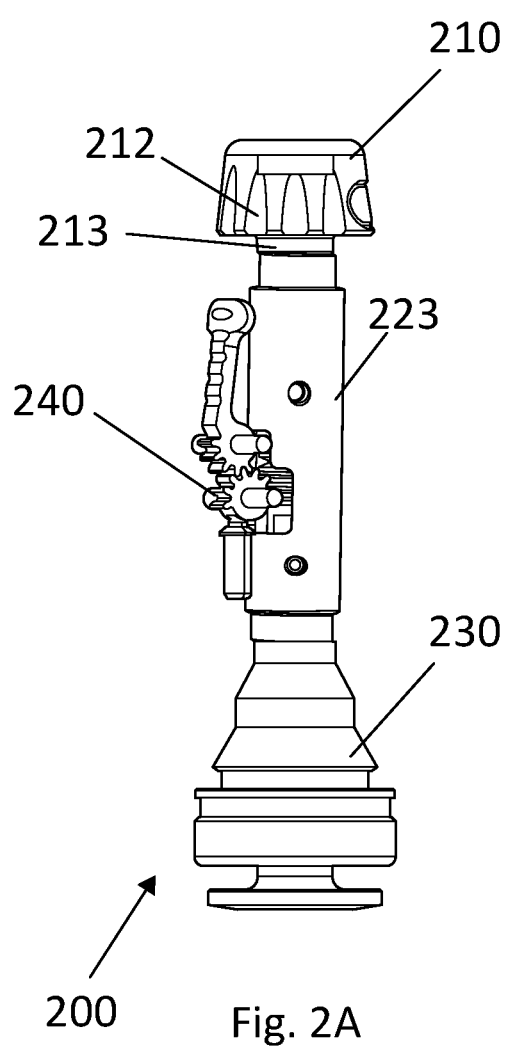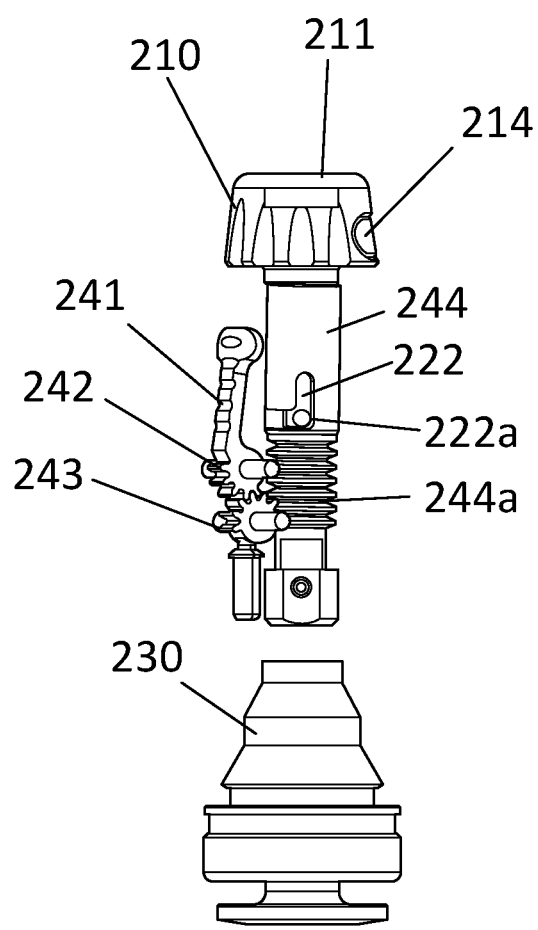
Fig. 2A
Fig. 2B

STYLET CONTROL HANDLES AND METHODS OF USING THE SAME

CROSS REFERENCE TO RELATED APPLICATIONS

The present patent application claims the benefit under 35 U.S.C. § 119(e) of U.S. Provisional Patent Application Ser. No. 63/128,606, filed on Dec. 21, 2020, the entirety of which is incorporated herein as though fully set forth.

BACKGROUND OF THE DISCLOSURE

The spine is critical in human physiology for mobility, support, and balance. Spinal injuries can be debilitating or catastrophic to patients. Even small irregularities in the spine can cause devastating pain and loss of coordination.

Surgical procedures are commonly performed to correct problems with displaced, damaged, or degenerated intervertebral discs. A wide spectrum of spinal procedures involve inserting bone anchors. During bone anchor insertion, the use of a stylet that extends beyond the distal tip of the bone anchor to be inserted may facilitate accurate and efficient insertion of the bone anchor. In particular, a stylet may be used during insertion of a bone anchor to avoid skiving and help surgeons plan insertion trajectory. In this context, skiving may include undesired displacement of a bone anchor tip relative to the bone without the tip entering the bone. There is an urgent need for convenient and efficient stylet retraction devices and methods which offer ease of manipulation by the surgeon, thereby imposing minimal interference to the screw insertion.

SUMMARY OF THE DISCLOSURE

Disclosed herein are stylet control handles for conveniently extending and retracting a stylet during bone anchor insertion. The stylet control handles disclosed herein can provide a retention mechanism to hold a stylet in place. The stylet control handles can have two modes of use. In the docking mode, the stylet can be retained at a fixed protrusion amount from the tip of the bone anchor. Malleting on the proximal surface of the cap may not push the stylet to extend beyond its fixed point. The stylet's protrusion from the bone anchor can advantageously allow the surgeon to dock the bone anchor and stylet on bone without the bone anchor skiving off the slick bony surface. In the extended mode, the stylet control handle may allow the surgeon to extend the stylet past the fixed point of the docking mode. Switching to the extended mode can unlock the stylet's translation relative to the bone anchor and malleting on the distal end of the handle can extend the stylet up to a predetermined distance in the distal direction. Extending the stylet past the bone anchor can advantageously allow the surgeon to confirm trajectory of the bone anchor, e.g., under fluoroscopy, before deployment of the bone anchor into bone.

As the stylet extends, a lever can pivot away from the handle. The lever can advantageously provide the user with a visual indication of how far the stylet has been extended. The lever can also provide a visual reminder for the surgeon to retract the stylet prior to inserting the bone anchor in bone. Squeezing or pivoting the lever back into a handle cover can simultaneously retract the stylet to its starting position, allowing for safe deployment of the bone anchor without the risk of the stylet kinking or bending. The lever's ergonomic location within the handle cover may promote retraction without significantly interrupting the natural surgical workflow. If desired, the user can mallet again on the proximal surface of the handle to re-deploy the stylet and again squeeze the lever to retract the stylet. Other methods of advancing the stylet besides malleting may also be used, including threaded and spring loading mechanisms. Other methods of retracting the stylet, such as different gear configurations or a cam may be used.

According to an aspect of the invention, a handle, e.g. a stylet control handle, is provided for extending and retracting a stylet during insertion of a bone anchor. The handle comprises a handle body; a cap assembly disposed at a proximal end of the handle body, and a cover disposed over at least a portion of the handle body. The cap assembly is releasably coupled to the stylet. A lever assembly is further provided, which comprises a lever which is operatively coupled to the cap assembly. The lever is configured to pivotably extend from an outer surface of the cover, e.g., at an adjustable angle. A portion of the cap assembly is configured to rotate and translate relative to the cover, and to move between a first, docking mode and a second, extended mode. In the second, extended mode, the lever is configured to pivot away from the handle body in response to translation of the portion of the cap assembly and the stylet in a distal direction. The stylet is further configured to retract in a proximal direction in response to the lever pivoting toward the handle body. Accordingly, the lever provides a visual indication of the position of the stylet.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2B show an exemplary embodiment of the stylet control handle disclosed herein; in this case, two different side views of the handle without the cover (FIG. 2A), and without the sleeve (FIG. 2B).

DETAILED DESCRIPTION OF THE DISCLOSURE

As disclosed herein, the term, "bone anchor" is interchangeable with or equivalent to the terms "anchor," "fastener," "bone fastener," "fixation screw," "pedicle screw," and any other analogous fixation means known to one of ordinary skill in the art. As disclosed herein, the term, "driver" is interchangeable with or equivalent to the term "screw driver," or any device that drives insertion of the bone anchor. As disclosed herein, the term "proximal direction" refers to the direction away from attachment of an element to the subject, while the term "distal direction" indicates the direction opposite the proximal direction and toward attachment of an element to the subject. As further disclosed herein, the term "stylet" may refer to a k-wire, or other probe for piercing or providing other functionality during bone anchor insertion.

As further disclosed herein, some embodiments relate to spinal fixation screws, bone anchors, fasteners, bone screws, and use of the same. In some embodiments, disclosed herein are stylet control handles for insertion and fixing bone anchors into a bony structure such a vertebra, and for automatically retracting a stylet during such insertion of a bone anchor. Ratchet retracting handles and methods of using the same are disclosed in U.S. patent application Ser. No. 17/412,613, filed Aug. 26, 2021, which is incorporated by reference as though fully set forth herein.

Figures 1A, 1B:
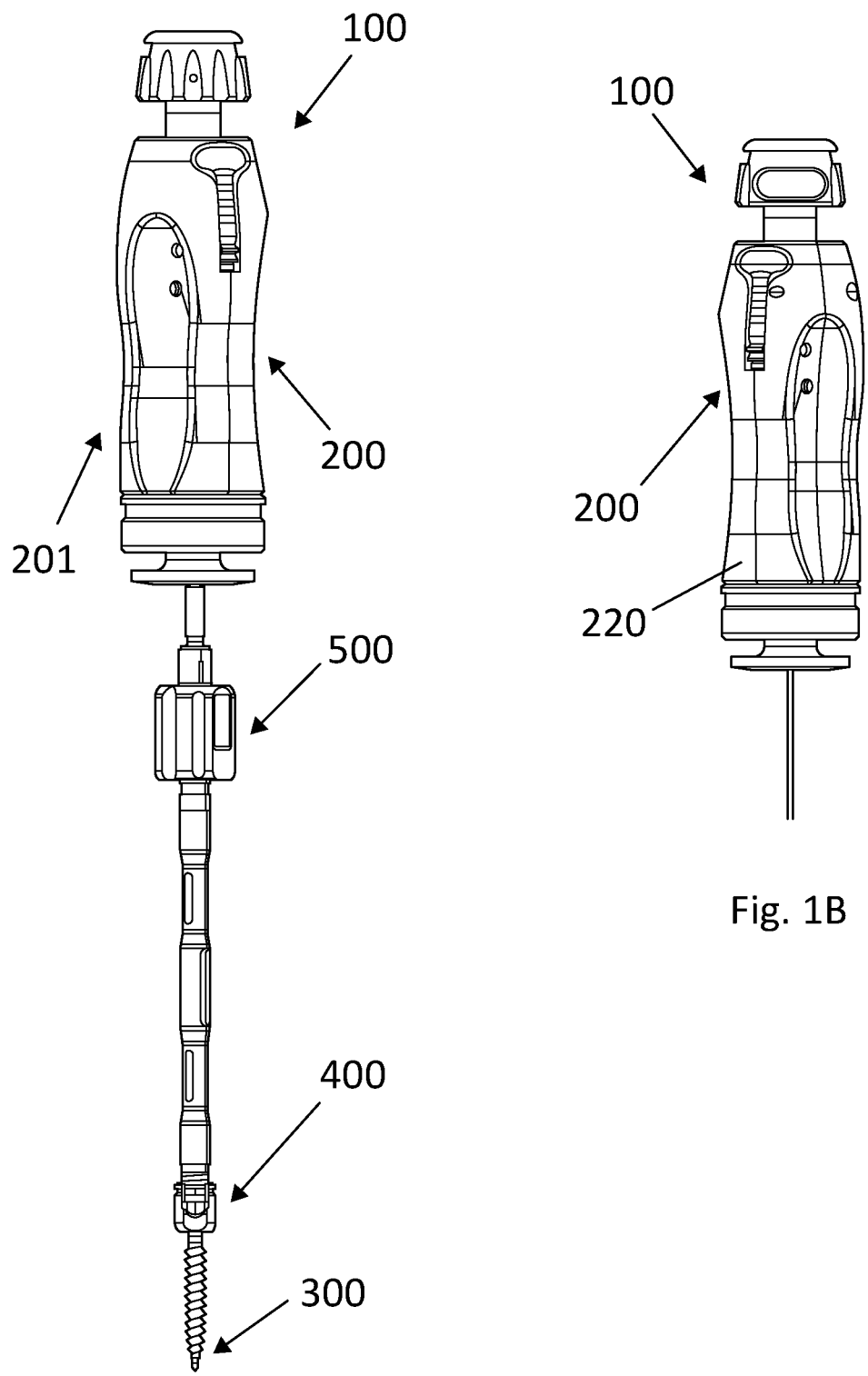
FIGS. 1A-1B show an exemplary embodiment of the stylet control handle disclosed herein; in this case, coupled with the stylet in a first side view (FIG. 1A) and a second side view without the screwdriver (FIG. 1B).

FIGS. 1A-1B show an insertion and retraction assembly 100 for inserting a bone anchor 400 into a bone. The insertion and retraction assembly 100 can include a stylet control handle 200, a stylet 300 (FIG. 1A), a bone anchor 400 (FIG. 1A) and a screw driver 500 (FIG. 1A). As shown in FIG. 1A, the stylet control handle 200 can be coupled to a proximal portion of the screw driver 500 for inserting the bone anchor 400. The stylet control handle 200 is used to maintain, deploy and retract the stylet 300 relative to the bone anchor 400. The stylet 300 can extend within a cannula or cavity within the bone anchor 400, and may be extended beyond a distal tip of the bone anchor 400.

In some embodiments, the stylet control handle 200 may have an elongated body 201 extending along a proximal to distal direction (FIG. 1A). As shown in FIGS. 2A-2B, handle 200 can include a cap assembly 210 comprising a cap 211 (FIG. 2B) disposed at a proximal end of the cap assembly 210, a knob 212 (FIG. 2A), and a cap body 213 (FIG. 2A) disposed distally relative to the cap 211 and the knob 212. Stylet control handle 200 may further include a cover 220 (FIG. 1B) disposed over at least a portion of body 201. In some embodiments, cover 220 (FIG. 1B) may also at least partly enclose the cap assembly 210, ratchet assembly 230 (FIG. 2A, discussed further herein), and lever assembly 240 (FIG. 2A, discussed further herein).

FIGS. 2A-2B and FIGS. 3A-3B show exemplary embodiments of the cap assembly 210. In some embodiments, the knob 212 is configured to rotatably actuate switching the stylet control handle 200 between different modes of operation, e.g., between a docking mode and an extended mode, as will be described herein. In some embodiments, the knob 212 can be configured to rotate relative to the cover 220 of the handle 200. The cap assembly 210 can further include a retention button 214 on the knob 212 that controls a retention element 217 (FIG. 3B) to releasably constrain the axial position of the stylet 300 relative to the cap assembly 210.

The proximal end of the stylet 300 may be maintained distal to the proximal end of the cap 211.

In some embodiments, the stylet control handle 200 may include a lever assembly 240, which is operatively coupled to the cap assembly 210. As shown in FIGS. 2A-2B, in a particular embodiment, a rack member 244 is connected proximally to the cap assembly 210, and provides the operative connection between the cap assembly 210 and the lever assembly 240. The cap body 213 can be rotationally and translationally fixed to rack member 244 (FIG. 2B, 3B). In various embodiments, the proximal end of rack member 244 may be coupled to a distal end of cap body 213. Rack member 244 may be configured to extend distally relative to cap assembly 210, within body 201 of handle 200.

As shown in FIG. 2B, rack member 244 can have a threaded part or a worm gear part 244a at its distal portion. The threaded or worm gear part 244a is configured to engage with at least one gear of lever assembly 240. In the embodiment of FIG. 2B, two gears 242, 243 are shown, as discussed further herein. The distal end of the rack member 244 may be configured to engage with, e.g., couple with, an inner shelf 221 (FIG. 3B) when the rack member 244 is rotated to a specific orientation relative to the inner shelf 221, e.g., in the extended mode.

The lever assembly 240 may include a lever 241 configured to pivot away from and toward the stylet control handle 200. The lever assembly 240 may include one or more gears 242, 243. One of the gears may be fixedly attached to the lever 241, e.g., lever gear or first gear 242. One of the gears may be coupled to the rack member 244 and a ball detent 245 (FIG. 5B), e.g., rack gear or second gear 243. One or more gears 242, 243 may have gear teeth on at least part of the circumference of the respective gear. In some embodiments, the gear(s) 242, 243 may have gear teeth only on a part of the circumference, e.g., about half of the circumference, or about 60% of the circumference. When the lever assembly 240 includes two gears 242, 243 (shown), the two gears 242, 243 are configured to rotate in opposite directions relative to each other. For example, one gear 242 may rotate in a clockwise direction while the other gear 243 rotates in a counterclockwise direction, or vice versa. The lever assembly 240 may include a lever gear or first gear 242 that is integrally formed with the lever 241. Alternatively, the lever 241 and the lever gear 242 may be two elements fixedly attached to each other, e.g. by a connecting member 241c (FIG. 6C). The lever gear or first gear 242 rotation and the pivoting of lever 241 can be simultaneous.

Figure 6A:
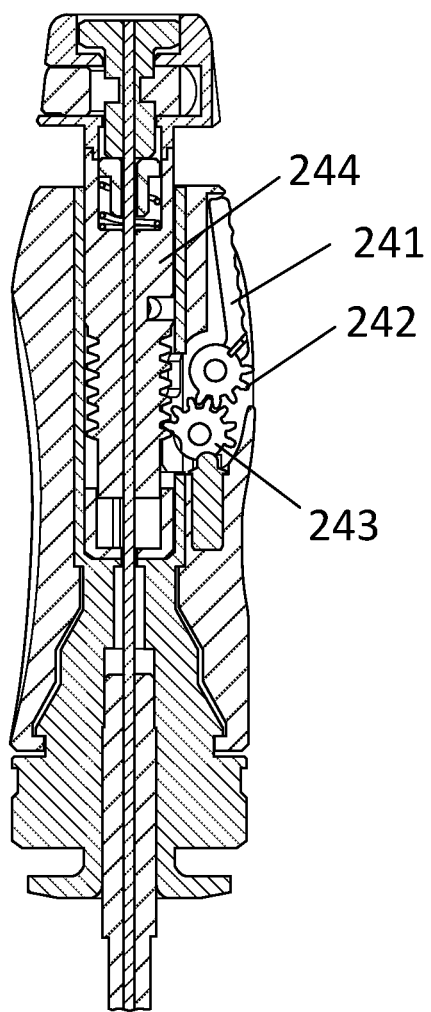
FIGS. 6A-6C show an exemplary embodiment of the stylet control handle disclosed herein; in this case, cross-sectional views of the stylet control handle before extended the stylet (FIG. 6A), in the process of extended the stylet (FIG. 6B), and toward the end of extended the stylet (FIG. 6C).
Figure 6B:
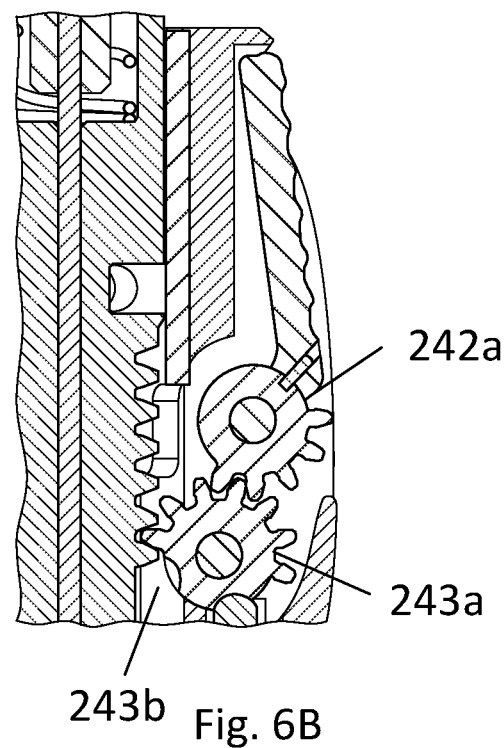

As shown in FIGS. 6A-6C, the lever assembly 240 can include a ball detent 245 configured to control rotation of the gears. Ball detent 245 limits pivoting of the lever 241 and consequently translation of the stylet 300. The ball detent 245 is configured to couple to one or more matching grooves 243a, 243b on the second gear 243, thereby limiting movement of the lever assembly 240 between the matching grooves 243a, 243b. The ball detent 245 can hold the lever assembly 240 in position when the ball detent 245 is coupled to one matching groove 243a, 243b, thus holding the stylet control handle 200 with the stylet 300 unextended or extended in the docking mode.

Figure 3A:
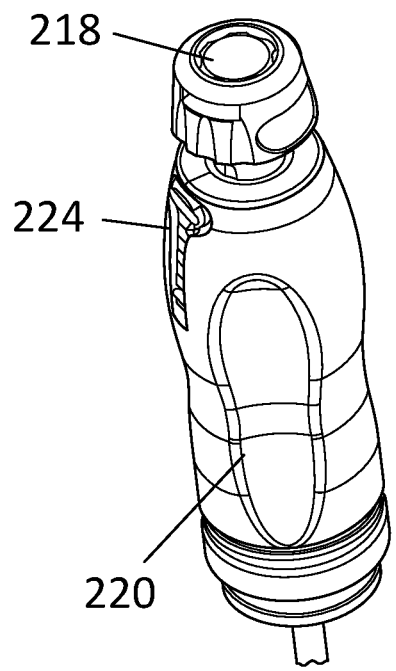
FIGS. 3A-3B show an exemplary embodiment of the stylet control handle disclosed herein in a docking mode; in this case, in a prospective view (FIG. 3A) and in a cross-sectional view (FIG. 3B).
Figure 3B:
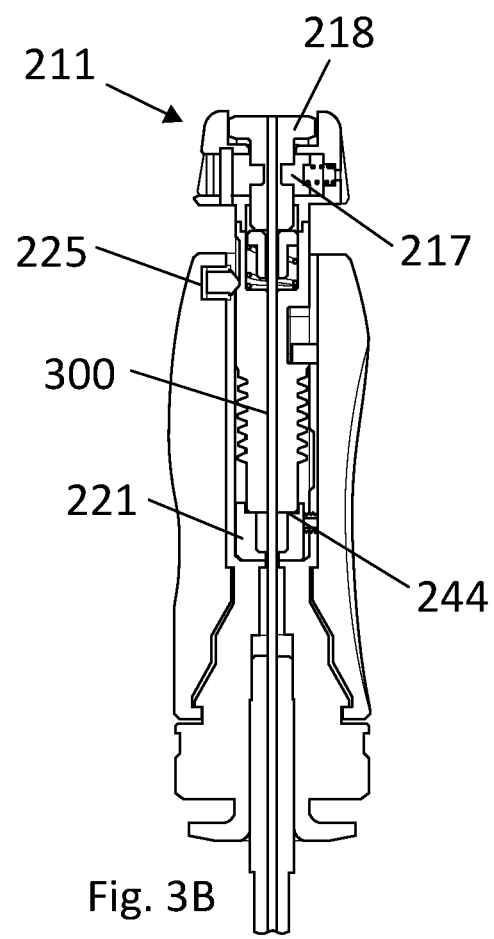
Figure 4A:
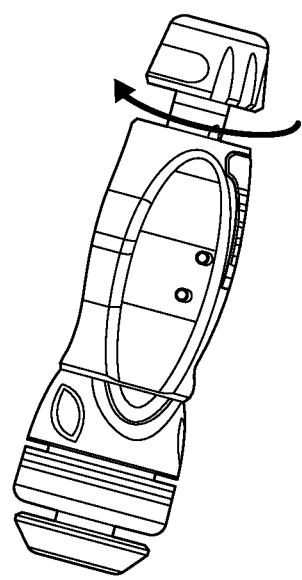
FIGS. 4A-4B show an exemplary embodiment of the stylet control handle disclosed herein in an extended mode; in this case, rotating from the docking mode to the extended mode (FIG. 4A) and malleting to extend the stylet in the extended mode (FIG. 4B).
Figure 4B:
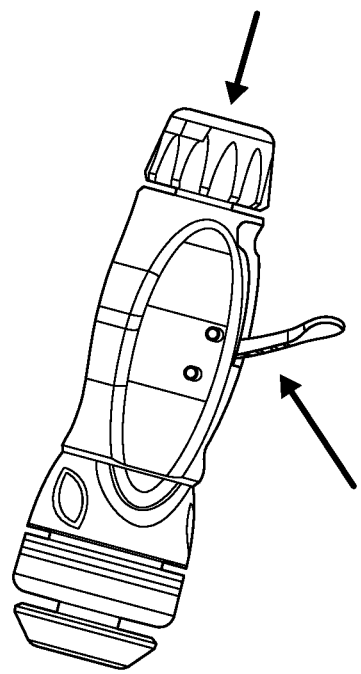

FIGS. 3A-3B show the stylet control handle 200 in the docking mode. As shown, the distal end of the rack member 244 (FIG. 3B) is not in a coupleable alignment with the inner shelf 221 (FIG. 3B). Rather, the distal end of rack member 244 is stopped by the proximal edge of the inner shelf 221 from any further distal movement. When a mallet or pushing force is applied on the cap 211, both the knob 212 and the cap 211 remain translationally fixed relative to the cover 220.

In the docking mode, the stylet 300, which is retained by the retention elements 217 in the cap assembly 210, can remain translationally fixed to the knob 212 and the cap 211, thus, the stylet 300 does not move distally. The distance that the stylet 300 may extend beyond the distal tip of the bone anchor 400 (FIG. 1A) in the docking mode can be predetermined or customized. The stylet 300 may extend to a fixed point in the docking mode. The fixed point can be, e.g., beyond the distal tip of the bone anchor 400 or flush with the distal tip of the bone anchor 400.

Figure 5A:
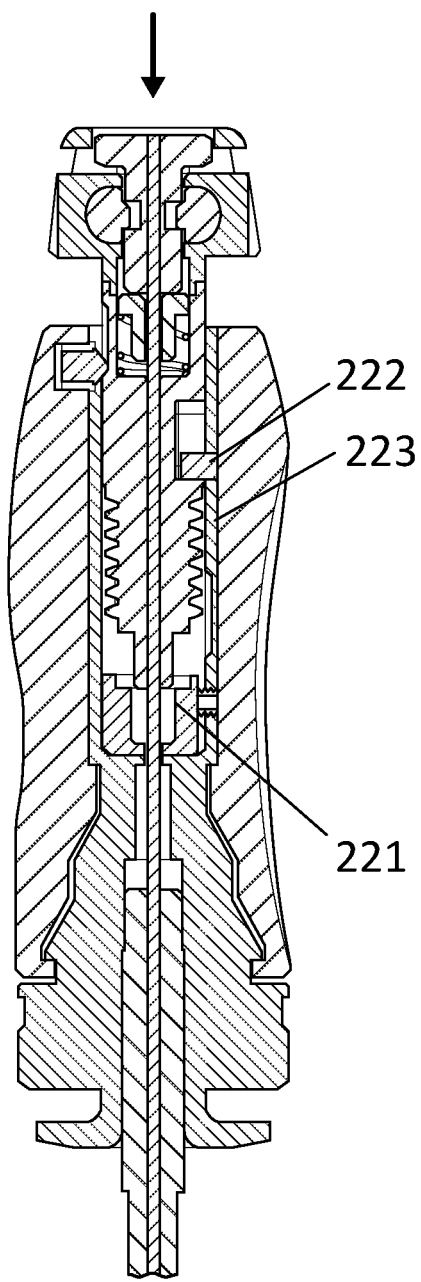
FIGS. 5A-5B show cross-sectional views of the stylet control handle disclosed herein in an extended mode.
Figure 5B:
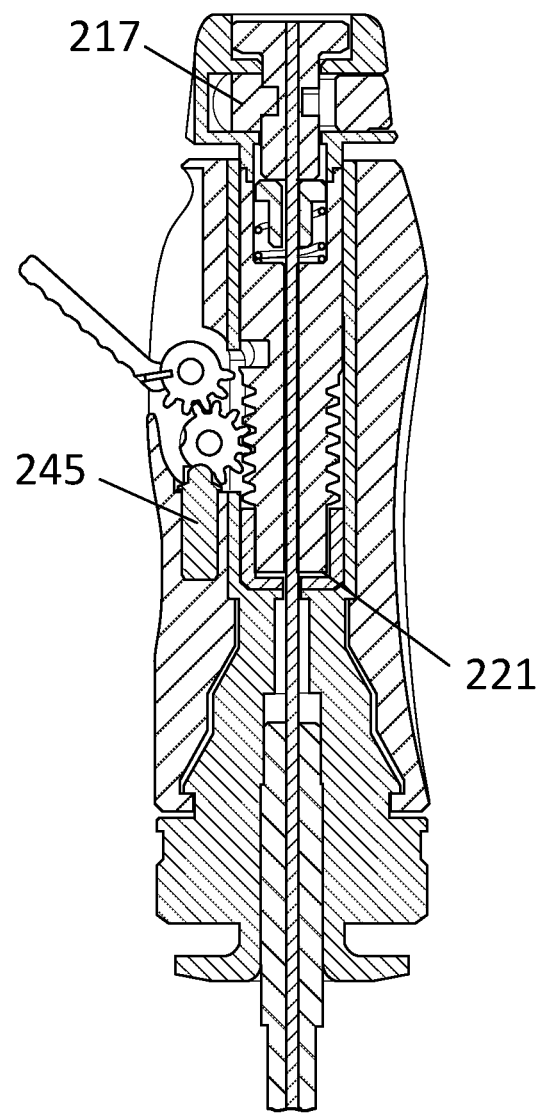
Figure 6C:
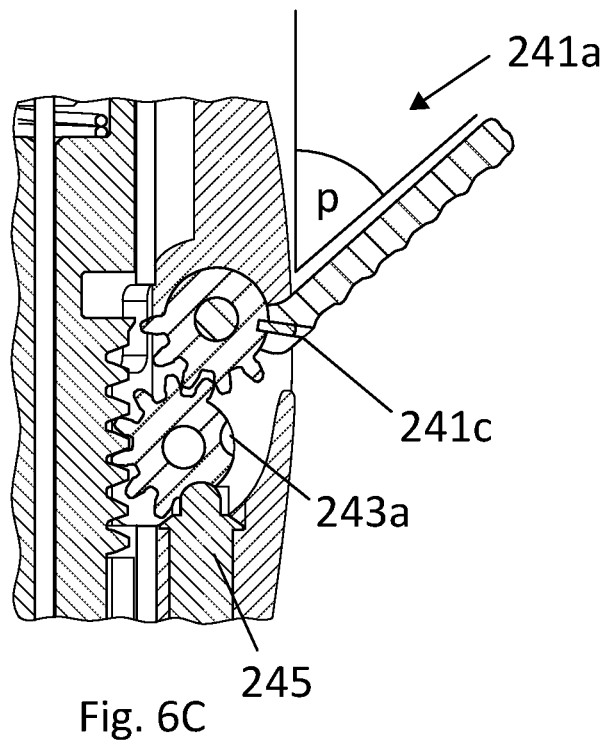

Switching from the docking mode into the extended mode may require rotation of the knob 212 in a clockwise or counter clockwise direction, for example, as shown in FIGS. 4A-4B and 5A-5B. Rotation of the knob 212 may be limited to only one direction by a pin 222 (FIGS. 2B, 5A) and a corresponding groove 222a (FIG. 2B) that restricts its rotation and/or translation. When the distal portion of the rack member 244 is properly aligned with the inner shelf 221, as shown in FIG. 5A, the rack member 244 can move distally by pushing the knob 212 distally until the rack member 244 abuts the distal end of the inner shelf 221, as shown in FIG. 5B. The stylet 300 that is translationally locked to the knob 212 thus can also move distally, and extend beyond the fixed point of the docking mode.

As can be seen in FIGS. 6A-6C, when the cap 211 is pushed to move distally, the rack member 244 which is translationally fixed to the knob 212 moves distally, and the rack or second gear 243 coupled to the rack member 244 is rotated in a first direction 243a. The lever or first gear 242 coupled to the second gear 243 rotates in a second direction 242a opposite the first direction. Simultaneously, the lever 241 pivots as the lever gear 242 rotates in a direction 241a away from the cover 211. When the rack member 244 abuts the distal end of the inner shelf 221 (FIGS. 5A, 6A), the rack gear 243 rotates so that the ball detent 245 couples with a groove 243b of the rack gear 243, and holds the gears 243 and the lever 241 in position. The lever 241 and the lever gear 242 may be fixedly attached to each other via a connector member 241c. The pivot angle p of the lever 241, shown in FIG. 6C, can provide a visual indication of the extended distance of the stylet 300. When the extended distance is larger, the pivot angle p is larger, and the lever 241 is further away from the cover 220. When the extended distance is smaller, the pivot angle p is smaller, and the lever 241 is nearer to the cover 220. The lever 241 also provides a visual reminder to the surgeon that the stylet 300 is extended and needs to be retracted before bone anchor placement.

To retract the stylet 300, in the extended mode, the lever 241 may be pushed back into the window 224 (FIG. 3A), which may be provided on the cover 220. The window 224 may be configured to receive lever 241 therewithin as shown in FIG. 1A. When the lever 241 is pushed back toward the cover 220, the lever gear 242 rotates in a direction opposite direction 242a, and the rack gear 243 also rotates in a direction opposite to its direction during stylet extension 243a. Retraction of the stylet 300 stops when the lever 241 is pushed back and coupled to the window 224, and the ball detent couples 245 to a groove 243a on the rack gear 243.

A ratchet assembly 230 (FIG. 2A) may be provided, which may be configured to couple with a screw driver 500 (FIG. 1A) for driving insertion of the bone anchor 400. The cover 220 can be rotationally fixed relative to the ratchet assembly 230 and to the lever assembly 240. The cover 220 may be translationally fixed relative to the ratchet assembly 230, and to the lever assembly 240 when extending or retracting the stylet. The cap 211 and/or the gear rack member 244 may rotate and/or translate relative to the cover 220. The lever 240, ball detent 245, and the gears 242, 243 do not rotate relative to the cover 220.

The cover 220 may include an element 225 (FIG. 3B) for providing tactile and audio feedback to a user (e.g., a surgeon or medical professional) during rotation of the cap 211. The cover 220 may include a sleeve 223 (FIG. 5A) that is fixedly attached to the cover 220, the ratchet assembly 230, or both. Sleeve 223 may further be disposed about rack member 244 within handle 200.

The retractable distance of the stylet 300 can be predetermined or customized. For example, it can be within a predetermined range or for a fixed value. As a non-limiting example, the retractable distance may be large enough so that when the stylet 300 is retracted, the tip of the stylet 300 is removed out of the patient. In some embodiments, the retractable distance may be in a range of about 0.1 mm to about 7 mm, or particularly between about 5 mm to about 12 mm, or particularly about 5 mm to about 15 mm. In some embodiments, the stylet control handle 200 may be reset to extend again subsequent to the retraction of the stylet 300.

In some embodiments, the stylet control handle 200 herein may extend and/or automatically retract a stylet 300 associated with a bone anchor 400 to be inserted. In the docking mode, the stylet 300 may extend beyond the distal tip of the bone screw 400 for a first distance. The first distance can be about 3 mm. The first distance can be any value in the range of about 0.1 to about 10 mm. In the extended mode, distal movement of the cap 211 and the knob 212 can cause the stylet 300 to be extended further beyond a distal tip of the bone screw 400 for a predetermined distance into a bone. For example, the predetermined distance is about 0.1 mm to about 7 mm. If the stylet's tip is 3 mm beyond the tip of the bone screw 400 in the docking mode. The stylet 300 can be further extended for another 7 mm in the extended mode. The extendable distance may total about 10 mm beyond the distal tip of the bone screw 400.

In some embodiments, the stylet control handle 200 may advantageously allow the stylet 300 to be retracted either in the docking mode or in the extended mode. In the docking mode, the lever 241 can be squeezed in further into the handle 200 in an opposite direction from that for stylet extension. This can cause opposite gear motions to the gear motion during stylet extension as shown in and described relative to FIGS. 6B-6C. The rack member 244 and the cap 211 can travel proximally thereby causing retraction of the stylet 300. Pulling up on the cap 211 proximally may click the rack member 244 into a retracted position.

Figure 7:
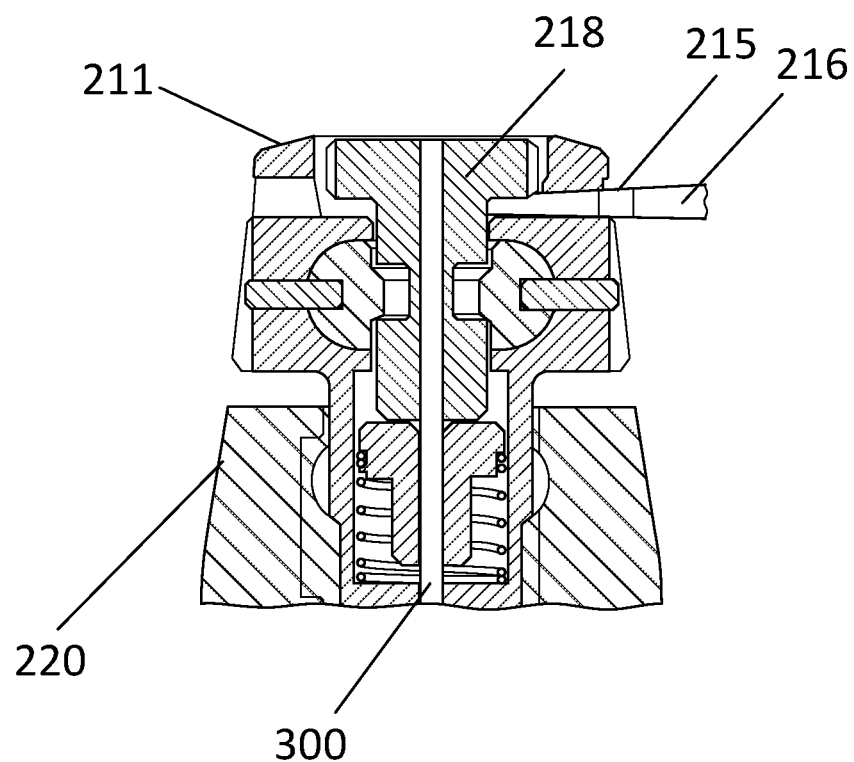
FIG. 7 shows an exemplary embodiment of the stylet control handle disclosed herein; in this case, a cross-sec tional view of the cap and a window for forcibly removing the stylet from the stylet control handle.

In some embodiments, the stylet control handle 200 disclosed herein can allow forcible removal of the stylet 300 from the handle 200, if the stylet 300 were to get stuck in bone. Referring to FIG. 7, in an exemplary embodiment, the cap 211 has a window 215 that provide access to an instrument 216 to contact a stylet holding element 218 within the cap, the stylet holding element 218 is fixedly attached to the retention element 217, and thus the stylet 300. The stylet 300 may be forcibly removed from the stylet control handle 200 when necessary by pushing the stylet holding element 218 proximally away from the cap 211.

In some embodiments, disclosed herein are methods for automatically retracting a stylet 300 associated with a bone anchor 400 during insertion of the bone anchor 400.

The methods may include one or more operations disclosed herein. The method may include providing a stylet control handle 200 disclosed herein to a user. The stylet control handle 200 can be couplable to a driver 500 for inserting the bone anchor 400. The method may include, in the extended mode, pushing the cap 211 or the knob 212 distally until the cap assembly 210 abuts the cover 220 or until the rack member 244 abuts an inner shelf 221. The method may include causing the lever 241 to pivot away from the cover 220 simultaneously while pushing the cap 211 or the knob 212 distally. The method may include, when at the docking mode or extended mode, retracting the stylet 300 proximally by pushing the lever 241 back into the window 224 of the cover 220.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +F7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A handle for extending and retracting a stylet during insertion of a bone anchor, the handle comprising:
    a handle body;
    a cap assembly disposed at a proximal end of the handle body, wherein the cap assembly is configured to be releasably fixed to the stylet;
    a cover disposed over at least a portion of the handle body; and
    a lever assembly comprising a lever,
        wherein the lever is operatively coupled to the cap assembly, and is configured to pivotably extend from an outer surface of the cover;
    wherein a portion of the cap assembly is configured to rotate relative to the cover, to move between a first, docking mode and a second, extended mode,
    wherein, in the second, extended mode, the lever is configured to pivot away from the handle body in response to translation of the portion of the cap assembly and the stylet in a distal direction, and
    wherein the stylet is configured to retract in a proximal direction in response to the lever pivoting toward the handle body.

2. The handle of claim 1, wherein the cap assembly comprises:
    a cap body;
    a knob coupled to and disposed proximally relative to the cap body; and
    a cap matingly engaged with a proximal end of the knob,
        wherein in the first, docking mode, the cap is constrained from translation in a distal direction relative to the cover, and the stylet is constrained from translation in a distal direction relative to a bone anchor, and
        wherein in the second, extended mode, the cap is configured to translate distally relative to the cover, and such distal translation of the cap causes the stylet to extend beyond a distal tip of the bone anchor.

3. The handle of claim 2, wherein the knob further comprises a retention button configured to releasably constrain an axial position of the stylet relative to the cap assembly.

4. The handle of claim 2, wherein the knob is configured to rotate relative to the cover to move between the first, docking mode and the second, extended mode.

5. The handle of claim 4, further comprising a rack member configured to couple the cap assembly to the lever assembly,
    wherein the rack member is coupled at a proximal end thereof to the cap assembly, and extends distally from the cap assembly,
    wherein the cap body and the rack member are rotationally and translationally fixed relative to one another, and
    wherein the rack member is disposed within the handle body.

6. The handle of claim 5, wherein the rack member further comprises a threaded portion at a distal end thereof.

7. The handle of claim 5, wherein the lever assembly further comprises a first gear configured to couple the rack member at a distal end thereof to the lever.

8. The handle of claim 7, wherein the first gear is coupled to the lever by a connector member, or the first gear is formed integrally with the lever.

9. The handle of claim 7, where in the lever assembly further comprises a second gear configured to couple the rack member to the lever via the first gear.

10. The handle of claim 9, wherein the first gear is configured to rotate in one of a clockwise or a counter clockwise direction, and the second gear is configured to rotate in the opposite of the clockwise or the counterclockwise direction.

11. The handle of claim 9, wherein each of the first gear and the second gear have gear teeth on at least part of the circumference of the respective gear.

12. The handle of claim 9, further comprising a ball detent configured to engage with the second gear, thereby limiting a pivoting motion of the lever assembly, and constraining an axial position of the stylet in the docking mode.

13. The handle of claim 12, wherein the ball detent is configured to directly limit rotation of the second gear and indirectly limit rotation of the first gear.

14. The handle of claim 12, wherein the ball detent is configured to engage with one or more corresponding grooves on the second gear.

15. The handle of claim 5, wherein the handle body further comprises an inner shelf, wherein the inner shelf is configured to matingly engage with a distal end of the rack member in the extended mode, and wherein the inner shelf is configured to not matingly engage with the distal end of the rack member, and to limit distal movement of the rack member in the docking mode.

16. The handle of claim 15, further comprising a pin disposed in a corresponding groove in the rack member, the pin being configured to limit rotation of the knob to one direction.

17. The handle of claim 1, wherein the cover further comprises a window having a shape complementary to that of the lever, the window being configured to receive the lever when it has pivoted toward the handle body.

18. The handle of claim 1, further comprising a ratchet assembly disposed at least partly within the cover, wherein the cover is rotationally fixed relative to the ratchet assembly and the lever assembly, and the ratchet assembly is configured to couple to a screw driver.

19. The handle of claim 18, further comprising a sleeve disposed about the ratchet assembly, wherein the sleeve is fixedly attached to an inner surface of the cover.

20. The handle of claim 1, wherein the cover further comprises a feedback element configured to provide a user with audio or tactile feedback as the cap assembly rotates or translates.

\* \* \* \* \*